United States Patent [19]

Binder et al.

[11] Patent Number: 5,527,796
[45] Date of Patent: Jun. 18, 1996

[54] THIENOTHIAZINE DERIVATIVES AND THEIR USE

[75] Inventors: Dieter Binder, Vienna; Josef Weinberger, Bad Hall, both of Austria

[73] Assignee: Chemisch Pharmazeutische Forschungsgesellschaft m.b.H., Linz, Austria

[21] Appl. No.: 198,781

[22] Filed: Feb. 18, 1994

Related U.S. Application Data

[63] Continuation-in-part of Ser. No. 73,541, Jun. 9, 1993, abandoned.

[30] Foreign Application Priority Data

Jul. 3, 1992 [AT] Austria ..................... 1360/92

[51] Int. Cl.[6] ................. A61K 31/38; C07D 513/04
[52] U.S. Cl. ........................ 514/226.5; 544/48
[58] Field of Search ................... 514/226.5; 544/48

[56] References Cited

U.S. PATENT DOCUMENTS

| | | | |
|---|---|---|---|
| 4,076,709 | 2/1978 | Hromatka et al. | 544/48 |
| 4,090,020 | 5/1978 | Binder et al. | 544/48 |
| 4,180,662 | 12/1979 | Pfister et al. | 544/48 |
| 4,187,303 | 2/1980 | Hromatka et al. | 544/48 |
| 4,224,445 | 9/1980 | Hromatka et al. | 544/48 |

OTHER PUBLICATIONS

Tanaka et al., Structure–Activity Relationships of the Thienothiazine Derivatives with Their Antiinflammatory, Analgesic and Ulcerogenic Effects and Their Inhibitory Effects on $PGE_2$ Biosynthesis, Chemical Abstracts 111:166771n (1989).

Hitzenberger et al., Pharmacokinetics of Lornoxicam in Man, Chemical Abstracts 115:21532h (1991).

*Primary Examiner*—Gary Geist
*Assistant Examiner*—Catherine Kilby Scalzo
*Attorney, Agent, or Firm*—Wenderoth, Lind & Ponack

[57] ABSTRACT

Thienothiazine derivatives of the formula

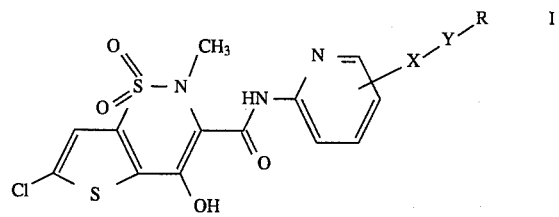

in which X denotes a single bond, a straight chain or branched carbon chain having 1–12 C-atoms in the chain, it being possible for this chain to contain one or more double or triple bonds and/or two or more heteroatoms, Y denotes a single bond, and R denotes a monocyclic or polycyclic, optionally partly hydrogenated aryl, heteroaryl, arlyoxy, arylaza, heteroarylaza, arylthio or heteroarylthio radical which can optionally be substituted by lower alkyl, mono- or poyhalogenated lower alkyl, perfluorinated lower alkyl, alkoxy or halogen, and their use.

7 Claims, No Drawings

THIENOTHIAZINE DERIVATIVES AND THEIR USE

This application is a continuation-in-part of Ser. No. 08/073,541, filed Jun. 9, 1993, now abandoned.

The invention relates to novel, therapeutically useful thienothiazine derivatives.

U.S. Pat. No. 4,180,662 discloses thienothiazine derivatives which cause cyclogenase inhibition.

The inventors have found novel thienothiazine derivatives which, while largely retaining the cyclooxygenase inhibition, cause a significantly increased inhibition of 5-lipoxygenase.

The invention accordingly relates to thienothiazine derivatives of the formula I

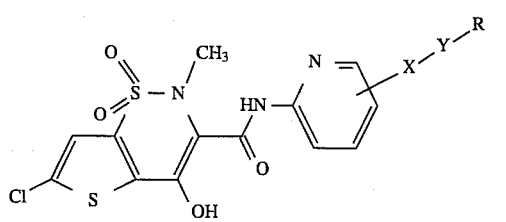

in which X denotes a single bond, a straight chain or branched carbon chain having 1–12 C-atoms in the chain, it being possible for this chain to contain one or more double or triple bonds and/or two or more heteroatoms, Y denotes a single bond, and R denotes a monocyclic or polycyclic, optionally partly hydrogenated aryl, heteroaryl, arlyoxy, arylaza, heteroarylaza, arylthio or heteroarylthio radical which can optionally be substituted by lower alkyl, mono- or polyhalogenated lower alkyl, perfluorinated lower alkyl, alkoxy or halogen.

Preferred compounds are those in which the substituent —X—Y—R is linked to the 6-position of the pyridine.

Lower alkyl denotes an alkyl radical having 1–4 C-atoms, for example a methyl radical, an ethyl radical, a propyl radical, an i-propyl radical, a butyl radical, an i-butyl radical or a t-butyl radical.

The term hetero atoms includes O, S and N.

Suitable mono- or polycyclic, optionally partially substituted aryl or heteroaryl radicals are 5–12-membered, optionally partly hydrogenated aromatic or heteroaromatic radicals, such as, for example, a phenyl, thienyl, furyl, pyrolyl, pyridinyl, pyrimidinyl, pyranyl, thiadiazinyl, azepinyl or benzofuryl or quinolinyl radical.

The thienothiazine derivatives according to the invention can be produced by reacting a compound of the formula II

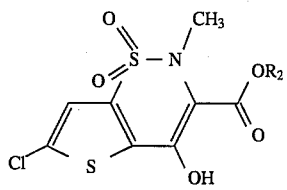

in which $R_2$ denotes a straight chain or branched alkyl group having 1–4 C-atoms, with a compound of the formula III

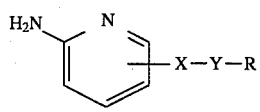

in which X, Y and R have the meaning mentioned above, and the resultant compounds of formula I are optionally converted into their pharmaceutically acceptable salts.

The process can preferably be carried out in one of the following ways, a) by dissolving a compound of the formula II in an inert solvent, such as diethylether, dioxane, toluene, benzene or the like and at a temperature between −20° C. and 100° C. adding an equivalent of a strong base, such as butyllithium or LDA, in an inert solvent, for example n-hexane, if appropriate under inert gas, adding 1–10 equivalents, preferably 1–5 equivalents, of a compound of the formula III to this salt solution, adding at least 1 equivalent of the strong base and stirring between 0.5 and 60 hours, preferably 1–48 hours, at −20° C. to 100° C., preferably 0° C. to 70° C., or b) by dissolving the compounds of the formula II and of the formula III in an inert high boiling solvent, such as toluene, xylene, pyridine, quinoline, dimethylformamide, dimethylsulfoxide or hexamethylenephosphoramide and heating this mixture at 100° C. to 200° C. for 1–30 hours.

The compounds of the formula (I) obtained in this reaction are acidic compounds and can be converted into their pharmaceutically acceptable salts in a customary manner using organic or inorganic bases.

Salt formation can be carried out for example by dissolving the compounds of the formula I in a suitable solvent, e.g. water, a lower aliphatic alcohol, tetrahydrofuran, dioxane, benzene, diethylether, dimethylformamide or dimethylsulfoxide, adding an equivalent of the desired base, ensuring a good mixing and, after salt formation is complete, stripping off the solvent in vacuo. The salts can optionally be further purified after their isolation, for example by recrystallizing.

Pharmaceutically tolerable salts are, for example, metal salts, in particular alkali metal salts and alkaline earth metal salts, such as sodium, magnesium or calcium salts. Other pharmaceutically acceptable salts are, for example, easily crystallizable ammonium salts. The latter are derived from ammonia or organic amines, such as e.g. mono- di or tri-lower(alkyl-, cycloalkyl-, or hydroxyalkyl)amines, lower alkylenediamines or (hydroxy-lower-alkyl or aryl-lower-alkyl)-lower alkyl-ammonium bases for example methylamine, diethylamine, triethylamine, dicyclohexylamine, triethanolamine, ethylenediamine, tri(hydroxymethyl)aminomethane, benzyltrimethylammoniumhydroxide and the like.

The compounds of the formula (II) and (III) are known from the literature and can be prepared analogously thereto by methods which are customary and familiar to a person skilled in the art.

The compounds of the formula (I) according to the invention and their salts are orally active and, in comparison to the compounds which are claimed in U.S. Pat. No. 4,180,662, such as for example, 6-chloro-4-hydroxy-2-methylo-N-(2-pyridyl)-2h-thieno[2,3-e]-1,2-thiazine-3-carboxamide-1,1-dioxide ("lornoxicam") surprisingly show a significantly higher inhibition of 5-lipoxygenase with extensive retention of cycloxygenase inhibition.

They are therefore particularly well suited for the treatment of complaints which are caused by the natural product of 5-lipoxygenase, namely leukotriene $B_4$, such as e.g. inflammation and pain in allergic asthma, arthritis, skin allergy, etc.

On account of these pharmacological properties, the novel compounds can be used on their own or mixed with other active substances in the form of customary pharmaceutical preparations as medicines for the treatment of disorders which are cured or alleviated by the inhibition of 5-lipoxygenase.

The invention furthermore relates to medicines which are used e.g. in the form of pharmaceutical preparations which contain the compounds of the formula (I) according to the invention and their salts mixed with a pharmaceutical, organic or inorganic excipient which is suitable for oral, enteral, parenteral and topical administration, for example water, gelatin, gum arabic, lactose, starch, magnesium stearate, talc, vegetable oils, polyalkylene gylcols, petroleum jelly and the like.

The pharmaceutical preparations can be present in solid form, e.g. as tablets, film tablets, coated tablets, suppositories, capsules or microcapsules, or in liquid form, e.g. as solutions, injection solutions, suspensions or emulsions, or in compositions with delayed release of the active substance. If appropriate, they can be sterilized and/or they contain auxiliaries such as preservatives, stabilizers or emulsifiers, salts for modifying the osmotic pressure or buffers.

In particular, pharmaceutical preparations can contain the compounds according to the invention in combination with other therapeutically useful substances. The compounds according to the invention can be formulated with these together with the above-mentioned auxiliaries and/or excipients to give combination preparations.

The novel compounds can be present in the compositions according to the invention in an amount of 4–200 mg per tablet, the remainder being a pharmaceutically acceptable filler.

A suitable dose for administration of the compounds is about 4–200 mg/kg per day, but other doses are also suitable, depending on the condition of the patient to be treated. The novel compounds can be administered in several doses and by the oral route.

EXAMPLE 1

6-Chloro-4-hydroxy-2-methyl-N-[3-(2-phenylethyl)-2-pyridyl)]-2H-thieno[2,3-e]- 1,2-thiazine-3-carboxamide-1,1-dioxide.

5.50 g (7,8 mmol) of methyl-6-chloro-4-hydroxy-2-methyl-2H-thieno[2,3-e]- 1,2,thiazine-3-carboxylate and 7.04 g (35.5 mmol) of 2-amino-3-(2-phenylethyl)pyridine are dissolved in 150 ml of abs. xylene and the mixture is heated to boiling for 5 hours. In the course of this, a total of 40 ml of liquid are removed by distillation and continuously replaced by fresh solvent. The cooled reaction mixture is filtered, and the crystallizate obtained is digested with methylene chloride and methanol, recrystallized from 150 ml of DMF and dried at 50° C. in vacuo. Yield: 5.34 g of yellow crystals (63% of theory) M.P.: 251°–252° C. (DMF, decomposition)

$^1$H-NMR: (CF3COOD) δ (ppm): 7.97 (d, 1H, Py-H6*); 7.86 (d, 1H, Py-H4*); 7,22 (dd, 1H, Py-H5); 6.96 (s, 1H, Th-H); 6.93–6.62 (m, 5H, Bz-H216); 2.90–2.55 (m, 4H, CH2—CH2); 2.61 (s, 3H, N—CH3)

$^{13}$C—NMR: (CF3COOD) δ (ppm): 171.5; 161.7; 151.8; 148.4; 145.5; 141.9; 139.4; 135.0; 133.4; 132.5; 131.6; 130.5; 126.5; 125.4; 112.7; 43.1; 37.8; 34.8

EXAMPLE 2

6-Chloro-4-hydroxy-2-methyl-N-[4-(2-phenylethyl)-2-pyridyl]2-thieno[2,3-e]-1,2-thiazine- 3-carboxamide-1,1-dioxide 0.96 g (3,10mmol) of methyl-6-chloro-4-hydroxy-2-methyl-2H-thieno[2,3-e]- 1,2-thiazine-3-carboxylate are dissolved in 21 ml of abs. toluene under a dry nitorgen atmosphere and treated at 2° C. with 1.24 ml (3.10 mmol) of a 2.5M solution of butyllithium in n-hexane. 1.23 g (6.20 mmol) of 2-amino-4-(2-phenylethyl)pyridine in 13 ml of abs. toluene are then added dropwise in the course of 15 minutes such that the temperature does not exceed 25° C., all substances are dissolved by heating to 50° C. for about 15 minutes and 2.48 ml (6.20 mmol) of a 2.5M solution of butyllithium in n-hexane are added dropwise at a temperature of 20°–35° C. in the course of 20 minutes.

The reaction mixture is stirred for 2 hours at room temperature, for 1.5 hours at 55° C. and overnight at room temperature, treated with 0.37 g (6.20 mmol) of glacial acetic acid and stirred with 40 ml of water for 1 hour at 1° C. and the precipitated crystals are filtered off and washed with cold water. The lithium salt obtained then is hydrolyzed with 50 ml of 2N HCl, the aqueous suspension is extracted three times with 50 ml of hot toluene each time and the organic extracts are evaporated. The crystals obtained are recrystallized from about 40 ml of benzene and dried in vacuo at 100° C.

Yield: 1.01 g of yellow crystals (68% of theory) M.P.: 214°–241° C. (benzene, decomposition) $^1$H-NMR: (DMSO) δ (ppm): 8.17 (d, 1H, Py-H6); 7.57 (s, 2H, Th-H, Py-H3); 7.35–7.12 (m, 6H, Py-H5, Bz-H2-6); 3.13–2.90 (m, 4H, CH2—CH2); 2.90 (s, 3H, N—CH3)

$^{13}$C-NMR: (DMSO) δ (ppm): 165.0; 164.2; 161.2; 148.6; 143.2; 140.2; 137.1; 137.0; 134.3; 128.3; 126.1; 122.6; 118.6; 114.9; 107.6; 39.1; 36.6; 34.7

EXAMPLE 3

6-Chloro-4-hydroxy-2-methyl-N-[5-(2-phenylethyl)-2-pyridyl]-2-H-thieno[2,3-e]- 1,2-thiazine-3-carboxamide-1,1-dioxide 1.93 g (6.2 mmol) of methyl-6-chloro-4-hydroxy-2-methyl-2H-thieno[2,3-e]- 1,2-thiazine-3-carboxylate are dissolved in 42 ml of abs. toluene under a dry nitrogen atmosphere and treated at 2° C. with 2.5 ml (6.2 mmol) of a 2.5m solution of butyllithium in n-hexane. 2.47 g (6.2 mmol) of 2-amino-5-(2-phenylethyl)pyridine in 23 ml of abs. toluene are then added dropwise at 20°–25° C. in the course of 15 minutes, the mixture is stirred at room temperature for about 15 minutes and 5.0 ml (12.5 mmol) of a 2.5M solution of butyllithium in n- hexane are added dropwise at a temperature of 20°–35° C. in the course of 20 minutes. The reaction mixture is then stirred overnight at room temperature, stripped for 30 minutes with 100 ml of 2N HCl and the precipitated crystals are filtered off and washed with cold water. The aqueous phase is cooled to 0° C. for a further 12 hours and the residual crystallized product is filtered off and washed with cold water. The combined fractions are dried over phosphorous pentoxide in vacuo at 50° C., recrystallized from 170 ml of ethylene gylcol monomethylether and dried in vacuo at 100° C. Yield: 1.89 g of yellow crystals (645 of theory) M.P:224°–227° C. (ethylene glycol monomethyl ether, decomposition) $^1$H-NMR: (DMSO) δ (ppm): 8.21–8.03 (m, 2H, Py-H3,6); 7.69 (d, 1H, Py-H4); 7.57 (s, 1H, Th-H), 7.37–7.12 (m, 5H, Bz-H2-6); 3.03–2.78 (m, 7H, CH2—CH2, N-CH3)

$^{13}$C-NMR: (CF3COOD) δ (ppm): 172.6; 161.8; 152.3; 149.2; 145.7; 142.4; 141.6; 140.7; 139.5; 135.5; 132.2; 132.0; 130.2; 126.4; 120.0; 112.7; 43.1; 39.5; 37.0

EXAMPLE 4

6-Chloro-4-hydroxy-2-methyl-N-[6-(2-phenyleth.,i)-2-pyridyl]-2H-thieno[2,3-e]- 1,2-thiazine-3-carboxamide-1,1-dioxide 1.43 g (4.61 mmol) of methyl-6-chloro-4-hydroxy-2-methyl-2H-thieno[2,3-e]- 1,2-thiazine-3-carboxylate are dissolved in 34 ml of abs. toluene under a dry nitrogene atmosphere and treated at 2° C. with 1.85 ml (4.61 mmol) of a 2.5M solution of butyllithium in n-hexane. 1.83 g (9.23 mmol) of 2-amino-6-(phenylethyl)pyridine in 17 ml of absolute toluene are added dropwise in the course of 20 minutes such that the temperature does not exceed 25° C., the mixture is stirred at room temperature for 15 minutes and 3.7 ml (9.23 mmol) of a 2.5M solution of butyllithium in n-hexane are added dropwise at a temperature of 20°–35° C. in the course of 20 minutes.

The reaction mixture is then heated to 70° C. for 2 hours, cooled, treated with 0.55 g (9.23 mmol) of glacial acetic acid and stirred at 0° C. for 1 hour, and the precipitated crystals are filtered off and washed with cold water. The lithium salt obtained is then hydrolyzed with 75 ml of 2N HCl, the aqueous suspension is extracted twice with 75 ml of hot toluene each time and the organic extracts are evaporated. The crystals obtained are recrystallized from about 70 ml of acetonitrile and dried in vacuo at 100° C. Yield: 1.33 g of yellow crystals (61% of theory) M.P.: 206°–208° C. (acetonitrile, decomposition) $^1$H-NMR: (CDCl3) δ (ppm): 7.37–7.11 (m, 7H, Bz-H2-6, Py-H3-4); 6.90 (d, 1H, Py-H5); 3.17–2.93 (m, 7H, C$\underline{H}$2—C$\underline{H}$2, N-C$\underline{H}$3)

$^{13}$C-NMR: (DMSO) δ (ppm): 164.9; 162.3; 153.4; 149.6; 143.9; 142.2; 140.0; 137.0; 134.5; 128.3; 126.2; 122.6; 117.6; 113.3; 108.3; 39.2; 35.3; 34.2

The following compounds were prepared in an analogous manner

| Ex. | Compound | M.P. (°C.) |
|---|---|---|
| 5 | 6-Chloro-4-hydroxy-2-methyl-N-[6-(2,4-difluorphenyl-oxy-methyl)]-2-pyridyl-2H-thieno[2,3-e]-1,2-thiazin-3-carboxamide-1,1,-dioxide | 174–177 |
| 6 | 6-Chloro-4-hydroxy-2-methyl-N-[6-(2-furyl)]-2-pyridyl-2H-thieno 2,3-e-1,2-thiazin-3-carboxamide-1,1,-dioxide | 207–209 (dec.) |
| 7 | 6-Chloro-4-hydroxy-2-methyl-N-[6-phenylethinyl]-2-pyridyl-2H-thieno[2,3-e]-1,2-thiazin-3-carboxamide-1,1,-dioxide | 222–229 (dec.) |
| 8 | 6-Chloro-4-hydroxy-2-methyl-N-[6-(3-phenylpropyl)]-2-pyridyl-2H-thieno[2,3-e]-1,2-thiazin-3-carboxamide-1,1,-dioxide | 159–162 |
| 9 | 6-Chloro-4-hydroxy-2-methyl-N-[6-(4-phenylbutyl)]-2-pyridyl-2H-thieno[2,3-e]-1,2-thiazin-3-carboxamide-1,1,-dioxide | 130–138 (dec.) |
| 10 | 6-Chloro-4-hydroxy-2-methyl-N-[6-(4-fluorphenoxy-methyl)]-2-pyridyl-2H-thieno[2,3-e]-1,2-thiazin-3-carboxamide-1,1,-dioxide | 172–174 (dec.) |
| 11 | 6-Chloro-4-hydroxy-2-methyl-N-[6-(4-phenoxymethyl]-2-pyridyl-2H-thieno[2,3-e]-1,2-thiazin-3-carboxamide-1,1,-dioxide | 169–172 (dec.) |
| 12 | 6-Chloro-4-hydroxy-2-methyl-N-[6-(2-benzo(b)furyl)]-2-pyridyl-2H-thieno[2,3-e]-1,2-thiazin-3-carboxamide-1,1,-diol | 254–256 (dec.) |
| 13 | 6-Chloro-4-hydroxy-2-methyl-N-[6-phenylmethoxy]-2-pyridyl-2H-thieno[2,3-e]-1,2-thiazin-3-carboxamide-1,1,-dioxide | from 176 (dec.) |
| 14 | 6-Chloro-4-hydroxy-2-methyl-N-[6-((E)-2-phenylethenyl)]-2-pyridyl-2H-thieno[2,3-e]-1,2-thiazin-3-carboxamide-1,1,-dioxide | 226–229 (dec.) |
| 15 | 6-Chloro-4-hydroxy-2-methyl-N-[6-phenylmethyl]-2-pyridyl-2H-thieno[2,3-e]-1,2-thiazin-3-carboxamide-1,1,-dioxide | 176–180 (dec.) |
| 16 | 6-Chloro-4-hydroxy-2-methyl-N-[6-phenyl]-2-pyridyl-2H-thieno[2,3-e]-1,2-thiazin-3-carboxamide-1,1,-dioxide | 207–208 (dec.) |
| 17 | 6-Chloro-4-hydroxy-2-methyl-N-[6-quinalinylmethoxy]-2-pyridyl-2H-thieno[2,3-e]-1,2-thiazin-3-carboxamide-1,1,-dioxide | 198–200 |
| 18 | 6-Chloro-4-hydroxy-2-methyl-N-[6-chinolinyloxymethyl]-2-pyridyl-2H-thieno[2,3-e]-1,2-thiazin-3-carboxamide-1,1,-dioxide | 156–160 |
| 19 | 6-Chloro-4-hydroxy-2-methyl-N-[6-(2-benzo(b)furyl-methoxy)[2-pyridyl-2H-thieno[2,3-e]-1,2-thiazin-3-carboxamide-1,1,-dioxide | 192–193 |
| 20 | 6-Chloro-4-hydroxy-2-methyl-N-[6-(2-benzo(b)thienyl-methoxy[2-pyridyl-2H-thieno[2,3-e]-1,2-thiazin-3-carboxamide-1,1,-dioxide | 199–201 |

EXAMPLE A

The formation of PGD2 by neutrophils was used as a measure for cyclooxygenase activity and the formation of LTB4 was used as a measure for 5-lipoxygenase activity.

Male Sprague Dawley rats (250–300 g) were injected with lambda carrageenan 1 mg intraperitoneally (dissolved in 0.5 ml dest.water) per animal. After 16 hours the rats were killed by exposure to diethylether. 15 ml ice cold Hanks balanced salt solution were injected i.p., neutrophils harvested by aspiration (10 ml), centrifuged (5 min, 100 g, 4° C.), the supernatant decanted and cells resuspended in HBSS at 4° C. to 5×10$^6$ cells/mi. 400 μl cell suspension (2×10$^6$ cells), 0.5 μl drugs dissolved in DMSO and 49.5 μl HBSS were incubated for 5 min at 37° C. Then 50 μl A23187 (2 μmol/l final conc.) were added followed by 5 min incubation at 37° C. The reaction was stopped by centrifugation for 30 s at 10000 g and the supernatant transferred to precooled plastic tubes and kept in an ice bath for max. 1 hour before starting RIA. PGD2 and LTB4 in the samples were measured after appropriate dilution with HBSS using commercial RIA kits.

Pharmacological Testing

Using the above mentioned methods the new compounds were tested. The inhibition of cyclooxygenase and of 5-lipoxygenase was measured.

|  | $IC_{50}$ (µmol/l) | |
| --- | --- | --- |
| Compound | PGD2 | LTB4 |
| A | 0.02 | >10 |
| 12 | 0.016 | 2.0 |
| according to ex. 4 | 0.19 | 2.7 |
| 14 | 0.18 | 4.3 |
| 13 | 0.15 | 5.1 |
| 11 | 0.12 | 7.3 |
| 10 | 0.45 | 4.8 |
| 9 | 0.75 | 1.9 |
| 8 | 0.51 | 4.2 |
| 7 | 0.41 | 3.7 |
| 17 | 0.66 | 2.0 |
| 20 | 0.35 | 3.2 |

The new compounds showed in addition to an inhibition of cyclooxygenase an inhibition of 5-lipoxygenase whereas lornoxicam (Compound A) inhibited only cyclooxygenase. The new compounds offer therefore a superior therapeutical principle for treatment of inflammatory diseases.

What we claim is:

1. A thienothiazine derivative of the formula

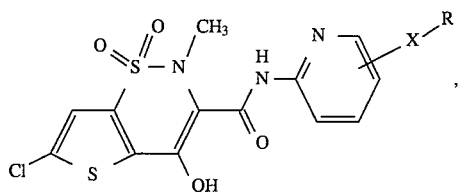

(I)

in which

X denotes a single bond, a straight or branched, optionally partially unsaturated carbon chain having 1–4 C-atoms in the chain, optionally containing one oxygen atom, and R is selected from the group consisting of phenyl, halogen-substituted phenyl, benzofuryl, furyl, quinolinyl and benzo(b)thienyl, under the proviso that —X—R does not denote phenyl.

2. 6-Chloro-4-hydroxy-2-methyl-N-[3-(2-phenylethyl)]-2-pyridyl)-2H-thieno[2,3-e]- 1,2-thiazine-3-carboxamide-1,1-dioxide.

3. 6-Chloro-4-hydroxy-2-methyl-N-[6-(2-benzo(b)furyl)]-2-pyridyl)-2H-thieno[2,3-e]-1,2-thiazine-3-carboxamide-1,1-dioxide.

4. 6-Chloro-4-hydroxy-2-methyl-N-[6-quinolinylmethoxy]-2-pyridyl-2H-thieno[ 2,3-e]-1,2-thiazin-3-carboxamide-1,1,-dioxide.

5. A compound according to claim 1, in which the —X—R is linked to the 6-position of the pyridine ring.

6. A pharmaceutical preparation containing a compound of the formula (1) according to claim 1 or a pharmaceutically acceptable salt thereof in combination with a customary pharmaceutical auxiliary and/or excipient.

7. A method of treating inflammation or pain in a patient suffering from inflammation or pain, which comprises administering to the patient a therapeutically effective amount of a compound according to claim 1.

* * * * *